United States Patent
Janik et al.

(10) Patent No.: US 12,350,414 B2
(45) Date of Patent: Jul. 8, 2025

(54) METHOD AND DEVICE FOR INTERMITTENT, PULSATING PROPORTIONING OF A DIALYSIS LIQUID MIXTURE

(71) Applicant: B. Braun Avitum AG, Melsungen (DE)

(72) Inventors: Waldemar Janik, Melsungen (DE); Eugen Schiller, Darmstadt (DE); Silvie Krause, Melsungen (DE)

(73) Assignee: B. Braun Avitum AG, Melsungen (DE)

( * ) Notice: Subject to any disclaimer, the term of this patent is extended or adjusted under 35 U.S.C. 154(b) by 1165 days.

(21) Appl. No.: 17/268,183

(22) PCT Filed: Aug. 28, 2019

(86) PCT No.: PCT/EP2019/072969
§ 371 (c)(1),
(2) Date: Feb. 12, 2021

(87) PCT Pub. No.: WO2020/043779
PCT Pub. Date: Mar. 5, 2020

(65) Prior Publication Data
US 2021/0244866 A1 Aug. 12, 2021

(30) Foreign Application Priority Data
Aug. 29, 2018 (DE) ...................... 10 2018 121 080.9

(51) Int. Cl.
*A61M 1/16* (2006.01)
(52) U.S. Cl.
CPC ........ *A61M 1/1656* (2013.01); *A61M 1/1607* (2014.02); *A61M 2205/18* (2013.01); *A61M 2205/3389* (2013.01)
(58) Field of Classification Search
None
See application file for complete search history.

(56) References Cited

U.S. PATENT DOCUMENTS

| 4,134,834 A | * | 1/1979 | Brous ................. A61M 1/1668 |
| | | | 210/127 |
| 4,202,760 A | | 5/1980 | Storey et al. |

(Continued)

FOREIGN PATENT DOCUMENTS

| CN | 104379189 A | 2/2015 |
| CN | 204425990 U | 7/2015 |

(Continued)

OTHER PUBLICATIONS

"Machine Translation of EP3100749", EP3100749, published 2016, 18 total pages. (Year: 2016).*

(Continued)

*Primary Examiner* — Jonathan M Peo
(74) *Attorney, Agent, or Firm* — Christopher A. Rothe; CM Law (57) ABSTRACT

A device and method that can be used to produce dialysis liquid for extracorporeal blood treatment. The device includes a main line for supplying water. An acidic and a basic fluid are introduced in specific dosages. The dosages are set by a control and regulation unit as a function of a chemical and/or physical parameter of the water/fluid mixture. The chemical and/or physical parameter is detected by a measuring device arranged at a section of the main conduit situated downstream of the introduction points for the acidic fluid and for the basic fluid. The control and regulation unit controls introduction of the acidic fluid and basic fluid so that only one of the acid and basic fluids is introduced into the main conduit over a predetermined period or a predetermined interval. Delivery and introduction of the basic fluid and acidic fluid take place alternately.

21 Claims, 8 Drawing Sheets

(56) References Cited

U.S. PATENT DOCUMENTS

| | | | |
|---|---|---|---|
| 2013/0049974 A1* | 2/2013 | Crnkovich | A61M 1/1662 340/657 |
| 2016/0000990 A1* | 1/2016 | Ritter | A61M 1/3663 210/101 |
| 2016/0051949 A1* | 2/2016 | Jansson | B01F 35/2202 366/162.1 |
| 2017/0304519 A1* | 10/2017 | Jonas | A61M 1/167 |
| 2018/0140762 A1 | 5/2018 | Kopperschmidt | |
| 2019/0015800 A1 | 1/2019 | Jansson et al. | |
| 2019/0192796 A1 | 6/2019 | Schranz et al. | |
| 2019/0388600 A1* | 12/2019 | Yuds | A61M 1/1601 |

FOREIGN PATENT DOCUMENTS

| | | |
|---|---|---|
| CN | 107949412 A | 4/2018 |
| DE | 2924182 C2 | 2/1985 |
| DE | 102014109369 A1 | 1/2016 |
| EP | 2988797 B1 | 3/2016 |
| EP | 3100749 A1 | 12/2016 |
| JP | 2001162148 A | 6/2001 |

OTHER PUBLICATIONS

Office Action received in Chinese Application No. 201980055557.6 dated Sep. 22, 2023, with translation, 32 pages.
German Search Report received in Application No. 10 2018 121 080.9 dated Mar. 18, 2019, 18 pages.
International Search Report received in Application No. PCT/EP2019/072969 dated Nov. 13, 2019, 4 pages.
Written Opinion received in Application No. PCT/EP2019/072969 dated Nov. 13, 2019, 13 pages.
Office Action received in Chinese Application No. 201980055557.6 dated Mar. 6, 2024, with translation, 28 pages.

\* cited by examiner

METHOD AND DEVICE FOR INTERMITTENT, PULSATING PROPORTIONING OF A DIALYSIS LIQUID MIXTURE

CROSS-REFERENCE TO RELATED APPLICATIONS

This application is the United States national phase entry of International Application No. PCT/EP2019/072969, filed Aug. 28, 2019 and published as WO 2020/043779A1 on Mar. 5, 2020, and claims the benefit of priority of German Application No. 10 2018 121 080.9, filed Aug. 28, 2018 and published as DE 10 2018 121 080 A1 on Mar. 5, 2020. The contents of International Application No. PCT/EP2019/072969 and German Application No. 10 2018 121 080.9 are incorporated by reference herein in their entireties.

FIELD

The invention relates to a method for producing a dialysis liquid, in which the basic and the acidic component are alternatingly added to the water or at least for one time in a time-staggered fashion as well as in intermittent and pulsating manner, so that due to this type of addition a single conductivity probe is sufficient to check the composition of the dialysis liquid to be mixed, the addition being effected by a negative pressure generated with the aid of at least one Venturi mixer.

BACKGROUND

In extracorporeal blood treatment, e.g. hemodialysis, hemofiltration, hemodiafiltration etc., a device is used for producing a dialysis liquid, which produces the required dialysis liquid from the basic components water, basic fluid and acidic fluid. The dialysis liquid produced is passed through the dialysis-side chamber of a dialyzer during the blood treatment of a patient. Via the semipermeable membrane of the dialyzer, toxins and water from the blood are absorbed by diffusion (hemodialysis) or diffusion in combination with convection (hemofiltration and hemodiafiltration), with the blood being passed through the blood-side chamber of the dialyzer.

During the extracorporeal blood treatment, the patient's blood to be treated is flushed in the dialyzer by the dialysis liquid. The basic component of the dialysis liquid usually is a substrate containing sodium hydrogen carbonate ($NaHCO_3$), and the second component (SK) usually is a solution containing sodium chloride (NaCl), potassium chloride (KCl), magnesium chloride ($MgCl_2$), calcium chloride ($CaCl_2$)), glucose ($C_6H_{12}O_6$) and acetic acid ($CH_3COOH$) and/or citric acid ($C_6H_8O_7$).

Dosing pumps and conductivity probes are generally used for the production or proportioning of the dialysis liquid. Here, a probe measures the conductivity of the $NaHCO_3$ after the addition using a first dosing pump (BICLF). Having added the acidic component by means of another dosing pump, another probe measures the conductivity of the entire dialysis liquid (ENDLF).

With conductivity-controlled proportioning, the quantities added are controlled on the basis of the measured conductivities. With volumetric proportioning, the conductivity probes are only used for checking purposes, since the proportioning is carried out directly via the dosing pump delivery rates. However, this requires precise knowledge of the composition of the components used.

Usually, two dosing pumps and at least two conductivity probes are used for producing a dialysis liquid. A first component, basic or acidic, is added to high-purity water via a first dosing pump, and the second component, acidic or basic, is added via a second dosing pump. The addition of the respective components is checked by one conductivity probe in each case. For safety-related monitoring of the composition, a second, independent channel and a third conductivity probe are usually also provided. Rotary vane piston pumps and diaphragm pumps are often used as dosing pumps, which are characterized by their non-continuous delivery.

The use of several dosing pumps, usually two, and several conductivity probes, usually two to three, for mixing the dialysis liquid according to the method of the conductivity-controlled proportioning is associated with high financial expenditures, since dosing pumps and conductivity probes are high-priced components of a device for extracorporeal blood treatment; what is more, their service life is limited by wear.

DE 10 2014 109 369 A1 discloses a system in which the acidic and the basic component are sucked into the main line through a negative pressure via switchable valves, wherein the negative pressure is generated by means of a pressure control valve arranged upstream of a mixing section in a main line in combination with a pump arranged downstream of the mixing section. In this way, both dosing pumps can be dispensed with. However, a pressure control valve is required, which is associated with comparatively high manufacturing and maintenance costs, and a more robust pump is required to generate the negative pressure.

Further, EP 3 100 749 A1 provides a dialysis machine comprising a line section for the production of dialysis fluid, in which the basic and acidic component are fed to a main line at junctions. This device does not provide pumps for delivering the components to a main line. Instead, a pump arranged downstream of the junctions in the main line in conjunction with a throttle valve arranged therein upstream of the junctions creates a negative pressure to suck in the respective components.

SUMMARY

The object of the present invention is therefore to overcome the known disadvantages in the production of a dialysis liquid for the extracorporeal blood treatment and to provide a method and device for producing a dialysis liquid from high-purity water, a basic component and an acidic component, which are distinguished in that the mixing and proportioning of the dialysis liquid is carried out much more efficiently and thus the unique costs as well as the running costs for the device and the method are significantly reduced.

A basic idea of the invention is thus to reduce the necessary technical effort in constructing a device and performing a method for producing a dialysis liquid, which is used in extracorporeal blood treatment, while maintaining technical reliability.

In other words, in comparison to the state of the art, the device according to the invention gets by with a smaller number of expensive sensory components and the method according to the invention is designed such that the measuring and control performance of the components installed is used so efficiently with the support of mathematical methods that an increased use of technical measuring and control equipment is superfluous and a further measuring device is completely replaced.

It can also be said that the total number of measuring devices required, for example measuring sensors, is reduced or a majority of measuring devices common in prior art is replaced by a clever arrangement of a single measuring device combined with a corresponding process control. In concrete terms, the streamlining of the technical equipment of a device for producing a dialysis liquid is provided such that only a single measuring device for recording at least one physical and/or chemical parameter, e.g. a conductivity probe, is used for monitoring and controlling the method for producing a dialysis liquid. Furthermore, the technical equipment of the device is further reduced by doing without a (dosing) pump for conveying the basic component (hereinafter also referred to as basic fluid) and the acidic component (hereinafter also referred to as acidic fluid).

The addition of the two fluids to the water, i.e. the production of the dialysis liquid, takes place via at least one Venturi mixer. This means that in a main line conducting the osmotic water or the fresh dialysis liquid, a conical constriction of the main line is provided immediately in front of an introduction point where the main line is connected to at least one supply line for the two fluids, and a conical widening of the main line is provided immediately after the introduction point or the main line is constricted at the introduction point. If necessary, the at least one supply line for the fluids can also narrow conically immediately before the introduction point. The profile of the constriction and the widening can be linear, tangential (spline-like) or similar. This creates a negative pressure in the main line at the introduction point according to the well-known Venturi principle, whereby the acidic and/or the basic fluid is/are sucked into the main line through the supply line connected to it. Preferably, the at least one Venturi mixer is designed as a single component to which hoses of the corresponding lines can be connected. The two fluids can be supplied to the main line via a common introduction point or via two different introduction points. This makes it possible to dispense with the cost- and maintenance-intensive dosing pumps for delivering the basic and acidic component or to use a smaller, cheaper pump for delivering the fresh dialysis fluid or the high-purity water, as said pump is not intended for generating a negative pressure.

Further, the addition of the two fluids to the water is carried out by the controlling of valves, which are arranged accordingly in the supply lines for the two fluids, and is carried out alternately, but at least once in a time-staggered manner. Due to this method it is possible to carry out the measurement of the at least one physical and/or chemical parameter of the water/fluid-mixture (also called component mixture) with a single measuring device, since in the measuring device for the water/fluid-mixture—at first having added a first fluid from the basic and acidic fluids to the water while equalizing the measured actual value with predetermined target values—the dosage or delivery rate of said first fluid can be checked and adjusted or controlled and for instance a reference value can be determined for the water/fluid-mixture consisting of water and the added first fluid. After preferred recording of the reference value, the second fluid from the basic and acidic fluids can be added to the water/fluid mixture, either so as to alternate with the first fluid, whereby in this case no reference value is required, since both fluid-water mixtures are calibrated individually and separately, or in addition to the first fluid under comparison with the reference value, without restricting the checking of the water/fluid mixture with a single measuring device.

As a whole, advantages according to the invention are achieved to the extent that, compared to the well-known devices and methods of producing a dialysis liquid for use in extracorporeal blood treatment, at least one measuring device can be dispensed with, which makes the expenditure of providing a device for producing dialysis liquid more economical and thus also reduces the cost of the method. Since sensors are expensive to purchase, the financial savings in relation to the overall cost are considerable if at least one of these parts is omitted. In addition, sensors have to be maintained and replaced from time to time, so that in addition to the monetary material costs, the personnel time required for support is also reduced. This applies equally to throttle valves for generating a negative pressure or to dosing pumps, which are used in known systems for conveying the acidic and basic fluid. Furthermore, the elimination of components means a reduction of dead spaces and a reduction of the risks of wear-related failure of the equipment.

The object is achieved by a device for producing a dialysis liquid for use in an extracorporeal blood treatment and comprising a main line for the supply of water, preferably osmotic or highly pure water, in the course of which an acidic fluid and a basic fluid are introduced each in a certain dosage or delivery rate. The dosage or delivery rate is set by a control and regulation unit depending on at least one chemical and/or physical parameter, preferably the conductivity, of the water/fluid mixture. The at least one chemical and/or physical parameter is detected by a measuring device, in particular a conductivity measuring probe, wherein a first, preferably only, measuring device is arranged at a section of the main line in each case downstream of the introduction point for the acidic fluid and downstream of the introduction point for the basic fluid. The control and regulation unit is designed to control the introduction of the acidic fluid and of the basic fluid at least temporarily (i.e., at least for a calibration operation) such that over a predetermined period or a predetermined interval only one fluid of the acidic and basic fluids is introduced into the main line. The device is characterized in that the control and regulation unit is adapted to control the delivery and introduction of the basic fluid and the delivery and introduction of the acidic fluid such that it takes place alternately, in particular in continuous alternating fashion (M1).

In other words, the object is achieved by a device for producing a dialysis liquid, which is a water/fluid mixture consisting of water and a basic fluid and an acidic fluid, for use in an extracorporeal blood treatment with a (single) measuring device for detecting at least one physical and/or chemical parameter of the water/fluid mixture. At least at the beginning of the method (calibration operation), the measuring device determines at least one parameter of a water/fluid-mixture first with isolated addition of a first fluid from the acidic and basic fluids to the water and optimally adjusts the dosage/delivery rate of this first fluid based thereon. Then, preferably a reference value can be determined for the water/fluid mixture which at this point in time consists of two components, before the second fluid from the acidic and basic fluids is introduced into the water/fluid mixture. At least one parameter of the water/fluid mixture consisting of three components now is determined and can be compared to the reference value, to determine deviations of the parameter from the reference value due to the addition of the second fluid and adjust its dosage/delivery rate accordingly. Alternatively, it is also possible to interrupt the delivery of the first fluid and to deliver the second fluid in order to adjust its dosage/delivery rate separately and optimally, whereupon the first fluid is switched on again with the delivery rate set previously. This makes it possible to check the mixture of water and two fluids with a single measuring device. The delivery of the water/fluid mixture can be carried out using familiar conveyance equipment such as pumps, possibly in combination with valves. If the calibration method is finished, i.e. if the delivery rates of the two fluids are set as described above, it is possible to switch to continuous delivery of the fluids.

It is already sufficiently and preferably provided that a single Venturi mixer is arranged at the device for the conveyance of the basic fluid and the acidic fluid. This can be done, for example, by a common line section. The supply lines for the two fluids, including the common line section, are designed without additional pumps, i.e. are free of pumps. The delivery of the water can also take place via a single pump, which is arranged at any point of the main line. For this purpose, preferably at least one valve, preferably a multi-way valve, may be arranged in the corresponding supply line or in the common line section for the introduction of the acidic fluid and/or the introduction of the basic fluid into the main line. If the basic and the acidic fluid are introduced into the main line preferably through two different supply lines and introduction points or through two different Venturi mixers, controllable Venturi mixers (in this case two) may be used as an alternative to the valves arranged in the supply lines. Such controllable Venturi mixers are adjustable with respect to their cross-sections. In this way, the negative pressure caused by the Venturi principle can be varied to suck in the concentrates. This allows to dispense with the valves and to further reduce the equipment's complexity. In other words, the delivery of the two fluids is done via at least one Venturi mixer, and the delivery rate is adjusted either by means of several switchable valves, variable valves (e.g. throttle valves), a multi-way valve or by way of several variable Venturi mixers.

Advantageously, at least one measuring device and at least one pump as well as one pressure control valve can be saved. The valves enable individual delivery rates for the components of the water/fluid mixture with a reduced number of pumps, as the delivery rate of the common pump and the valve opening and closing times of the valves can be combined accordingly.

Further preferred, it is possible to provide a further measuring device immediately downstream of the first measuring device which is adapted to capture at least one physical and/or chemical parameter of the water/fluid mixture flowing through the main line.

In order to quickly and reliably identify conspicuous or faulty measurement results as such, the parameters measured at the first measuring device are compared with the parameters measured at the further measuring device. The further measuring device is connected to a separate monitoring unit. In other words, the measurement results of the first measuring device are checked by a second measurement on the further measuring device, thus increasing the safety during production of the dialysis liquid.

In principle, it is not necessary to arrange for a separately provided mixing device in addition to the Venturi mixer, such as a static mixer or a chamber of a chamber-based balancing system. However, it may be preferable to provide such an additional and supportive mixing device, preferably downstream of the first and/or further measuring device and further preferably downstream of the introduction point for the acidic fluid and the introduction point for the basic fluid.

The mixing of the water/fluid mixture after addition of the basic fluid and/or acidic fluid into a mixing device leads to a more representative, i.e. more accurate, measurement result at the measuring device. This means that slight fluctuations in concentration, which may still be present after the addition of the basic and/or acidic fluid to the water by the Venturi mixer, can be further homogenized during mixing by an additional mixing device, i.e. can be compensated. The mixer used may be a static mixer such as a Kenics mixer, or the chamber of a chamber-based balancing system. A mixing or homogenization of the fluid mixture directly downstream of the addition point(s) (introduction point(s), orifice point(s)) favors the accuracy of the measurement results of the measuring equipment. Turbulences caused by the mixing process can be resolved in the best possible way over the longest possible flow distance between the outlet from the mixing device and the passage through the measuring unit. The arrangement downstream of the further measuring equipment is particularly advantageous if the addition of the basic fluid and/or of the acidic fluid is coded, for example via the conductivity. The basic fluid typically has a lower conductivity than the acidic fluid. In order to be able to measure the conductivity of the fluid mixture passing through the measuring device as accurately as possible, in particular the temporal progression of the conductivity, the water/fluid mixture should not pass through a mixing device before passing through the measuring device. However, in order to reduce fluctuations in concentration for the further course of the method or use of the produced dialysis liquid as far as possible, such a case provides for a mixing after the water/fluid mixture has left the measuring device.

The device may preferably be adapted to carry out the method described below.

Furthermore, the invention relates to a method of producing a dialysis liquid which contains the three components, namely water, basic fluid and acidic fluid, for use in an extracorporeal blood treatment on a device for extracorporeal blood treatment comprising the steps conveying water, preferably osmotic or high-purity water, via a main line, conveying a basic fluid and introducing it into the main line at a first introduction point by a first Venturi mixer, conveying an acidic fluid and introducing it into the main line at a first introduction point by a first Venturi mixer or at a second introduction point by a second Venturi mixer, measuring at least one physical and/or chemical parameter, preferably the conductivity and especially preferred the temperature-compensated conductivity, of the water/fluid mixture, which consists of water, the acidic fluid and/or the basic fluid, by means of a first measuring device, preferably a conductivity probe, and especially preferred a temperature-compensated conductivity probe, and adjusting the delivery rates for the water, the acidic fluid and/or the basic fluid by a control and regulation unit as a function of the measured value detected.

In doing so, the measuring of the at least one physical and/or chemical parameter is performed preferably by means of a single measuring device which is located at a section of the main line downstream of the introduction point for the acidic fluid and of the introduction point for the basic fluid. The control and regulation unit at least temporarily (i.e. at least for a calibration operation) controls the introduction of the acidic fluid and/or the basic fluid such that over a predetermined period or a predetermined interval only one of the acidic and basic fluids is introduced into the main line and the parameter for setting the dosage/delivery rate of this one fluid is measured in clocked fashion or on a continuous basis.

In other words, in the method according to the invention of producing a dialysis liquid for use in extracorporeal blood treatment at a device for extracorporeal blood treatment, the composition of the water/fluid mixture which, consisting of high-purity water, a basic component and an acidic component, corresponds to the dialysis liquid, is checked and controlled on the basis of the at least one measured physical and/or chemical parameter. First, a first fluid from the basic and acidic fluids is introduced into the water in isolated manner and the water/fluid mixture made up of two components, namely water and the first fluid of the basic and acidic fluids, is measured before the second fluid of the basic and acidic fluids is introduced into the water or the water/fluid mixture of two components and measured. The measurement of the at least one physical and/or chemical parameter of the water/fluid-mixture consisting of water, the basic fluid and/or the acidic fluid is carried out exclusively at one flow point which in the direction of the water flow is located downstream of the introduction point for the basic fluid and the introduction point for the acidic fluid in the main line.

If the addition of the fluids to the water or water/fluid-mixture is realized by at least one switchable valve with the help of at least one non-adjustable Venturi mixer, this is preferably done intermittently and in pulsating manner, so that the fluids are conveyed in bursts with interruptions, as described in more detail below with reference to FIG. 4. Alternatively, controllable valves can be used, or the valves can be omitted completely and controllable Venturi mixers can be used instead. This has an advantageous effect on the mixing with the water or water/fluid mixture. Furthermore, due to this type of addition, a single measuring device is sufficient to check the composition of the dialysis liquid to be mixed. It is advantageous here that at least one measuring device common in prior art can be saved.

Preferably, the delivery and introduction of the basic fluid and the delivery and introduction of the acidic fluid can take place alternately, in particular in continuously alternating manner. Preferably, the delivery rates of the water and/or of the fluids conveyed can be readjusted or adapted with each cycle and especially preferred at any time of the delivery process. It is also possible to maintain the previously set delivery rate of the simultaneously conveyed component (e.g. water) during the modification of the delivery rate of a mixture component (e.g. the conveyed fluid).

Alternatively, the delivery of the basic fluid and the delivery of the acidic fluid can be preferably carried out in parallel in a time-staggered manner.

By starting the pumping and the initially isolated introduction of a fluid from the basic and acidic fluids into the water and adjusting the delivery rate of this one fluid and/or of the water to a defined target value for the water/fluid mixture, the required delivery rate of the one fluid and/or of the water can be calculated and/or adjusted more reliably and faster than with simultaneous delivery or simultaneous delivery start of the basic and acidic fluid and introduction into the water. After the first fluid from the basic and acidic fluids has been introduced into the water and the water/fluid mixture been measured as described above, a reference value for this fluid addition can be recorded as a first alternative. Subsequently, the second fluid can be added to the previously calibrated water/fluid mixture and the resulting parameter deviations from the reference value can be recorded, which can be used as a basis for the dosage/delivery rate of the second fluid.

As a second alternative, the delivery of the first fluid can be interrupted and replaced by the delivery of the second fluid after the dosage/delivery rate of the first fluid has been adjusted. As soon as its dosage/delivery rate is set by measuring of the parameter, the first fluid can be switched on again with the dosage/delivery rate previously set. This allows the delivery rates of all three mixture components, namely water, the basic fluid and the acidic fluid, to be controlled with a single measuring device when the second fluid from the basic and acidic fluids is subsequently introduced into the water/fluid mixture.

Preferably, when adapting a delivery rate of a fluid from the basic and acidic fluids for the period of the adaptation, in particular from the change in the delivery rate until reaching the new target value of the water/fluid mixture, the delivery rate of the other fluid from the basic and acidic fluids set before the adaptation can be maintained or its delivery can be paused.

It is especially preferred that the adjustment of a delivery rate of one component can be performed while maintaining the delivery rates of the other components that are simultaneously delivered. This applies in particular to the case of the parallel delivery of the two fluids.

The delivery rate to be changed can be set more reliably and quickly if the delivery rate to be newly set during readjustment is the only changed variable in the water/fluid mixture. This also makes it possible to adapt a delivery rate for one component while the delivery of the other two components is continued with the previously set delivery rates. This applies in particular to the case of the parallel delivery of the two fluids.

According to the invention, the comparison with the target value includes a control. With the control, the actual value and target value are compared with each other. The control deviation is formed and then transferred to a controller, which then determines a corresponding manipulated variable (here the valve opening and closing times, a degree of opening of the valves or a setting of the adjustable Venturi mixer, possibly dependent on a pump delivery rate). By way of example, possible controllers include discontinuous multipoint controllers, P controllers, PI controllers, PID controllers, fuzzy controllers, adaptive controllers, hybrid controllers and/or controllers based on artificial neural networks. The target delivery rates can be determined by calculation or else by analytical methods.

Further preferred, the water/fluid mixture can be lead past the device for extracorporeal blood treatment in the event of changing or newly setting at least one target value for the water/fluid mixture until the target value is reached again at least once. This can also be used for isolated control of the individual dosages or delivery rates at regular intervals. In this way, an otherwise threatening alkalosis or acidosis of the patient can be prevented. After such a short-term interruption of the delivery and addition of the basic and/or acidic fluids, the one whose delivery and addition was interrupted can be additionally delivered and added to the extent that the physiological composition to be achieved continues to result in the long-term average for the fluid mixture.

All relevant process parameters can be considered as target values, e.g. mixing ratios of the components, electrolyte concentrations in the mixture, pH value of the mixture, pumping volume and/or delivery volume.

Preferably, in a case where a defined time span is exceeded for reaching at least one delivery rate of the water/fluid mixture and/or a delivery rate is set which exceeds a defined limit value, a warning can be issued at the device for extracorporeal blood treatment.

In this way it can be ensured that a wrong fluid was not accidentally connected to the device and that the connection of the fluid was done correctly. Furthermore, it can be detected in this way whether the storage container, e.g. a canister, of the connected fluid is empty and needs to be replaced. A warning signal can be given acoustically, visually or haptically.

Further preferred, the method may further include a step of measuring at least one physical and/or chemical parameter of the water/fluid mixture, which consists of water, the basic fluid and/or the acidic fluid, by means of a further measuring device, preferably a conductivity probe and especially preferably a temperature-compensated conductivity probe, which is arranged on the main line immediately downstream of the first measuring device, and that in a case in which a deviation between the parameter measured at the first measuring device and the parameter measured at the further measuring device exceeds a defined limit, a warning is output at the device for extracorporeal blood treatment.

A further measurement, it could be said a control measurement, is used to verify the measurement made at the first measuring device and is supposed to increase the safety during production of the water/fluid mixture or dialysis liquid. In addition to conductivity probes, preferably those with temperature sensors, ion-selective electrodes or optical measuring means such as devices for laser-induced plasma spectroscopy, are conceivable first and further measuring devices.

In addition, the water/fluid mixture, which consists of water, the basic fluid and/or the acidic fluid, can preferably be mixed by means of at least one mixing device, preferably a static mixer, which is provided in addition to the Venturi mixer.

This serves the homogenization of the fluid mixture and leads to more accurate and reliable measurement results. Possible mixing devices are, for example, Kenics mixers or chambers of chamber-based balancing systems. If the method is carried out without the additional mixing device, averaging or filtering of the measured parameters, e.g. conductivity, by means of analog or digital filtering may be used to determine the measured value more precisely.

Preferably, the mixing device may be a chamber of a chamber-based balancing system and the physical and/or chemical target value of a water/fluid mixture consisting of water, the basic fluid and/or the acidic fluid may be defined in such a way that it can be realized mathematically within a unit of time corresponding at most to one balance chamber switchover.

This allows better intermixing in the balance chamber. In cases in which the physical and/or chemical target value cannot be realized within one time unit which corresponds at most to one balance chamber switchover, the target value can be approached in several stages, whereby an individual target value stage can be defined in such a way that it can be realized mathematically within one time unit which corresponds at most to one balance chamber switchover.

Especially preferred, the addition of the basic fluid and of the acidic fluid can be coded, preferably by using a Barker code.

For the addition of the basic fluid, the conductivity or sodium concentration to be achieved exhibits a lower value at the measuring device than the conductivity or sodium concentration to be achieved while adding the acidic fluid. The signal or the measured value of the basic fluid can then be coded according to the Barker code with "−1" and the signal or the measured value of the acidic fluid with "+1". The signal resulting at the measuring device can then be processed or evolved by appropriate mathematical means, whereupon conclusions can be drawn about the added quantities of the individual fluids.

In order to determine the type of concentrate supply actually fluid-connected to the system, e.g. a canister, a cartridge or a central concentrate supply, a pressure sensor is preferably provided immediately upstream of each valve, preferably at the same height of each valve, respectively. The pressure sensors are designed to measure the prevailing pressure within the line section between the storage container and the valve after connection of the concentrate supply and when the valve is closed. Based on the value measured by the pressure sensors, the control and regulation unit adjusts properties of the controller like the P-, I- and/or D-part for adapting the individual dosages of the acidic and basic liquid.

Further preferred, in case a canister is determined as the type of concentrate supply actually fluid-connected to the system, a filling level of the concentrate contained in the canister can be determined by means of the pressure sensors. According to the invention, a haptic, acoustic or visual warning signal can be issued at the device for extracorporeal blood treatment if the filling level determined in the canister falls below a previously set threshold value. In this way, it can be detected at an early stage whether the canister of the connected fluid needs to be replaced. Thus, production of the dialysis liquid can be continuously guaranteed and dialysis therapy does not have to be interrupted.

Preferably, the method can be adapted to be able to be carried out with the device described above.

The methods described above are based on the conductivity-controlled proportioning of the fluid mixture or dialysis liquid. It is of course also possible to produce the dialysis liquid according to the principle of volumetric proportioning, provided that the valve opening and closing times of the at least one valve provided in the supply lines or in the common line section for the acid and the basic fluid and the composition of the fluids are known exactly. The measurement of the at least one physical and/or chemical parameter is carried out also with this principle by only one measuring device. The measured at least one physical and/or chemical parameter serves here only as control and not as an actual value of a regulation scheme.

A proportioning unit, which in particular has the Venturi mixer(s) and/or the at least one valve for adjusting the delivery rates of the fluids to be proportioned and, if necessary, associated connections and lines, can be located within a single dialysis machine. Alternatively, the proportioning unit may be provided as a separate module outside at least one dialysis machine and may be used, if necessary, to produce the dialysis fluid for several dialysis machines.

BRIEF DESCRIPTION OF THE DRAWING FIGURES

The invention is described in more detail below using preferred exemplary embodiments with reference to the attached drawings.

DETAILED DESCRIPTION

Figure 1A:
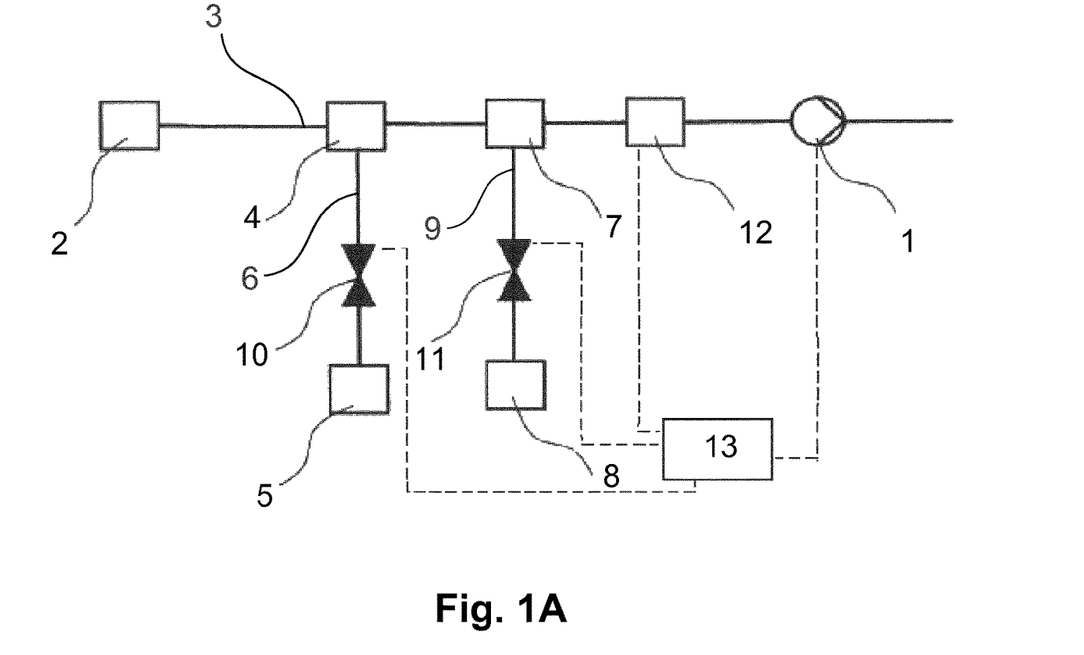
FIG. 1A shows a schematic representation of a first device according to the invention.

FIG. 1A shows a first embodiment, according to the invention, of the device for producing a dialysis liquid. A (first), optionally adjustable pump 1 delivers/sucks water from a reservoir 2, which may be a container such as a canister or a continuous source, via a main line 3 towards pump 1. A first Venturi mixer 4, which is located at a first introduction point in the main line 3, conveys a basic fluid from a first storage container 5, which may be a canister or a cartridge, via a first supply line 6 to the main line 3, where the first supply line 6 opens into the main line 3 at first introduction point. A second Venturi mixer 7, which is arranged at a second introduction point in the main line 3, conveys an acidic fluid from a second storage container 8, which may be a canister among other things, via a second supply line 9 to the main line 3, where the second supply line 9 opens into the main line 3 at the second introduction point. The addition of the basic fluid and the acidic fluid in the water is done by operating two controllable valves 10, 11, which are arranged accordingly in the first supply line 6 and the second supply line 9. Downstream of the introduction point (orifice point) of the supply line 6 in the main line 3, there is arranged a measuring device 12, which may be a conductivity probe among other things, preferably a conductivity probe with temperature sensor for temperature-compensated conductivity determination. The measuring device 12 measures at least one physical and/or chemical parameter of the passing water/fluid mixture. A control and regulation unit 13 processes the signals of the measuring device 12 and controls the pump 1 as well as the valves 10, 11.

Figure 2A:
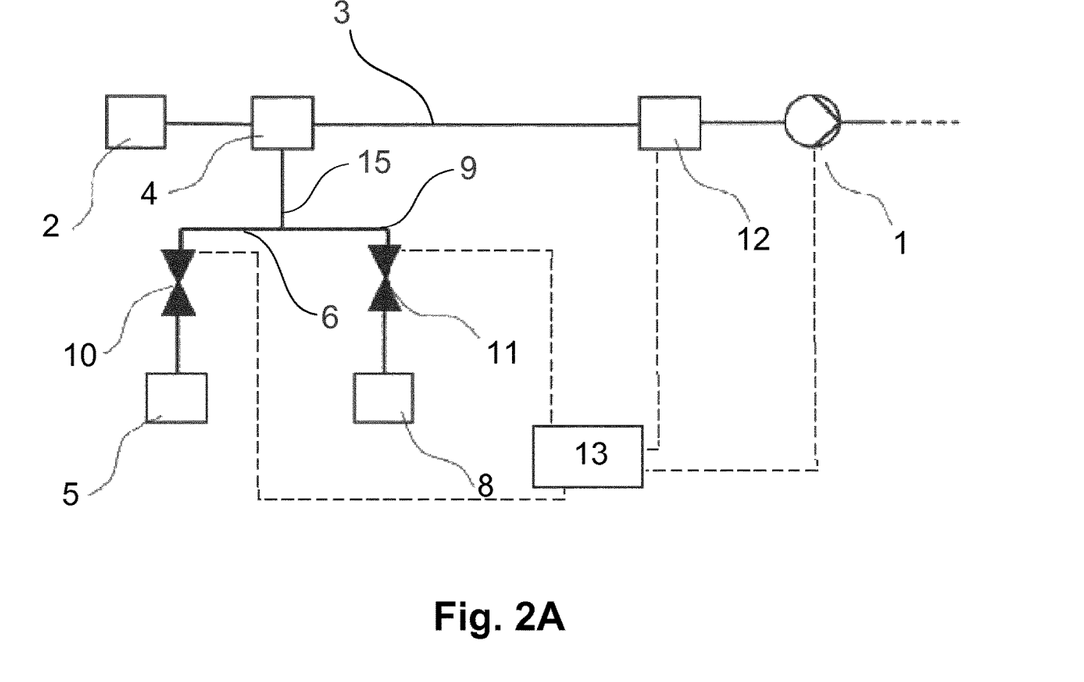
FIG. 2A shows a schematic representation of a second device according to the invention.

FIG. 2A shows a second embodiment according to the invention of the device for the production of a dialysis liquid. The basic structure and the reference numerals from the first embodiment remain unchanged, so that in the following only differences between the first and second embodiment are discussed. Instead of the Venturi mixers 4, 7, a single Venturi mixer 4 conveys the basic fluid and the acidic fluid to the main line 3, where the supply line 6 and the supply line 9 converge to a common line section 15 which opens into the main line 3 at a single introduction point via the single Venturi mixer 4 (i.e., the first and the second introduction point correspond to each other). The (controllable) valve 10 is provided at the supply line 6 and the (controllable) valve 11 is provided at the supply line 9. The addition of the basic fluid and the acidic fluid to the water is done by operating (opening and closing) the valves 10 and 11. Downstream of the point where the common line section 15 opens into the main line 3, the measuring device 12 is arranged. A control and regulation unit 13 processes the signals from the measuring device 12 and controls the pump 1 and the valves 10 and 11.

The dosing in the second embodiment is performed in interaction with the valves 10, 11 so that when one of the fluids is to be conveyed and introduced, the valve on the supply line of the fluid to be conveyed is open. The valve on the other supply line remains closed during this time. If both fluids are to be added in parallel, this can also be done via the corresponding control of the valves.

Figure 1B:
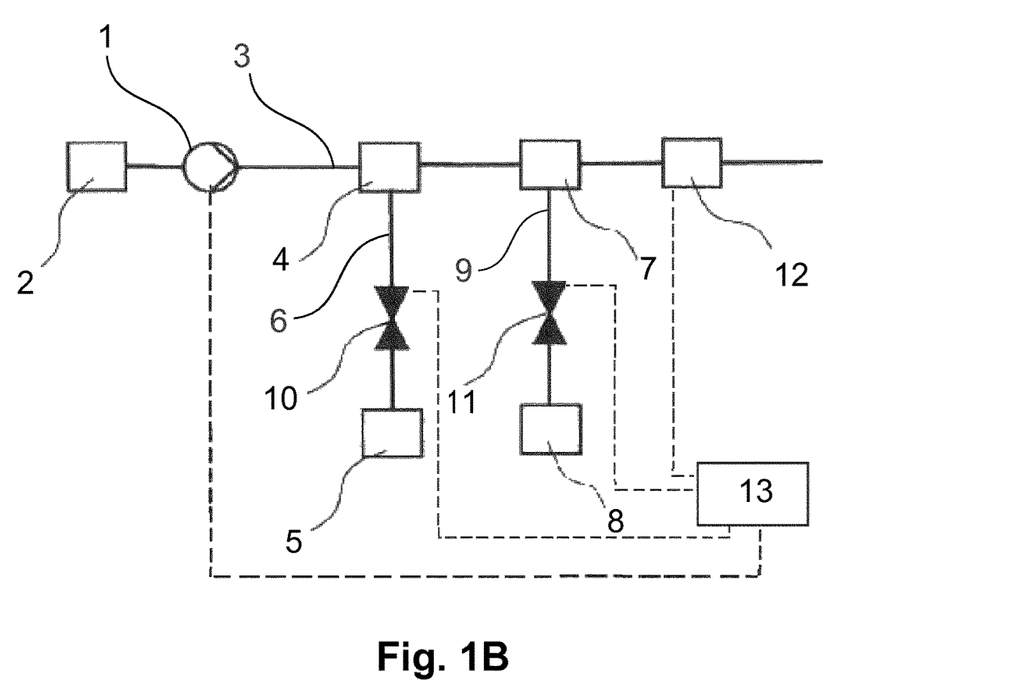
FIGS. 1B and 2B show variations of the first and second device according to the invention, respectively.
Figure 2B:
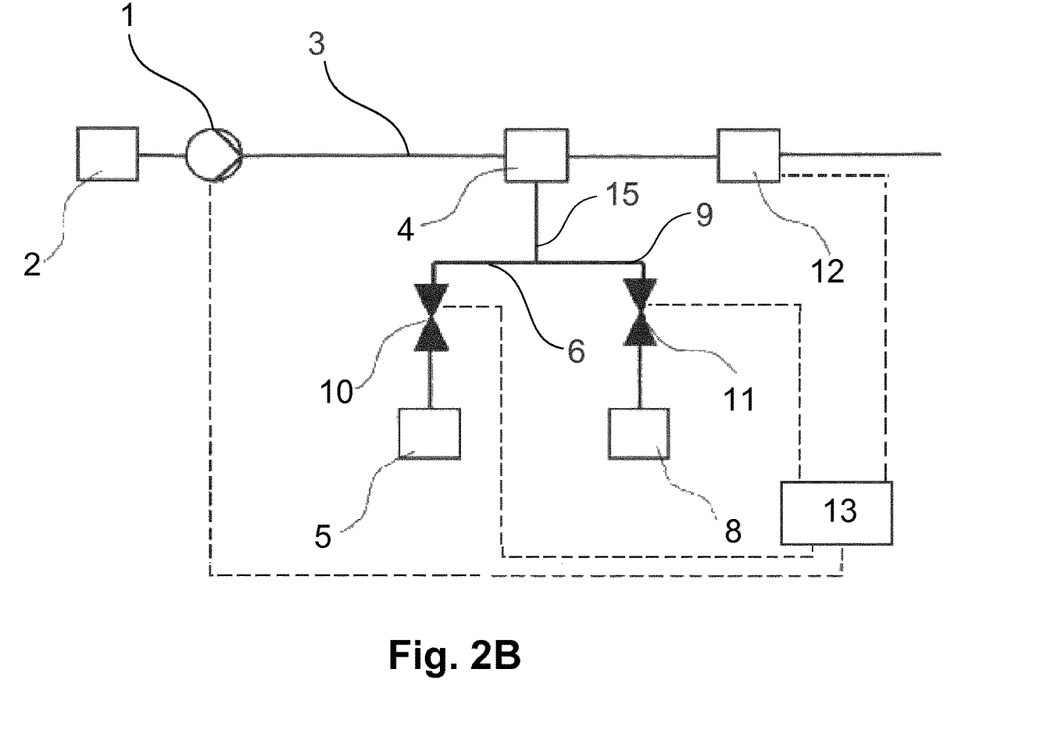

FIG. 1B and FIG. 2B show variations of the devices shown in FIG. 1A and FIG. 2A which differ from these in that the pump 1 is located to be upstream of the introduction point(s).

Figure 3:
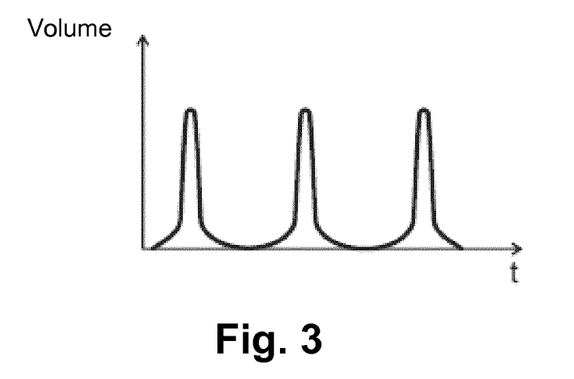
FIG. 3 shows a diagram of a pulsating pump delivery from the state of the art.

FIG. 3 shows a diagram illustrating an addition quantity (volume) as a function of time (t). This is a pulsating or intermittent conveyance from the state of the art in which the addition quantities of the basic or acidic components are not supplied evenly but in pulsed fashion.

Figure 4:
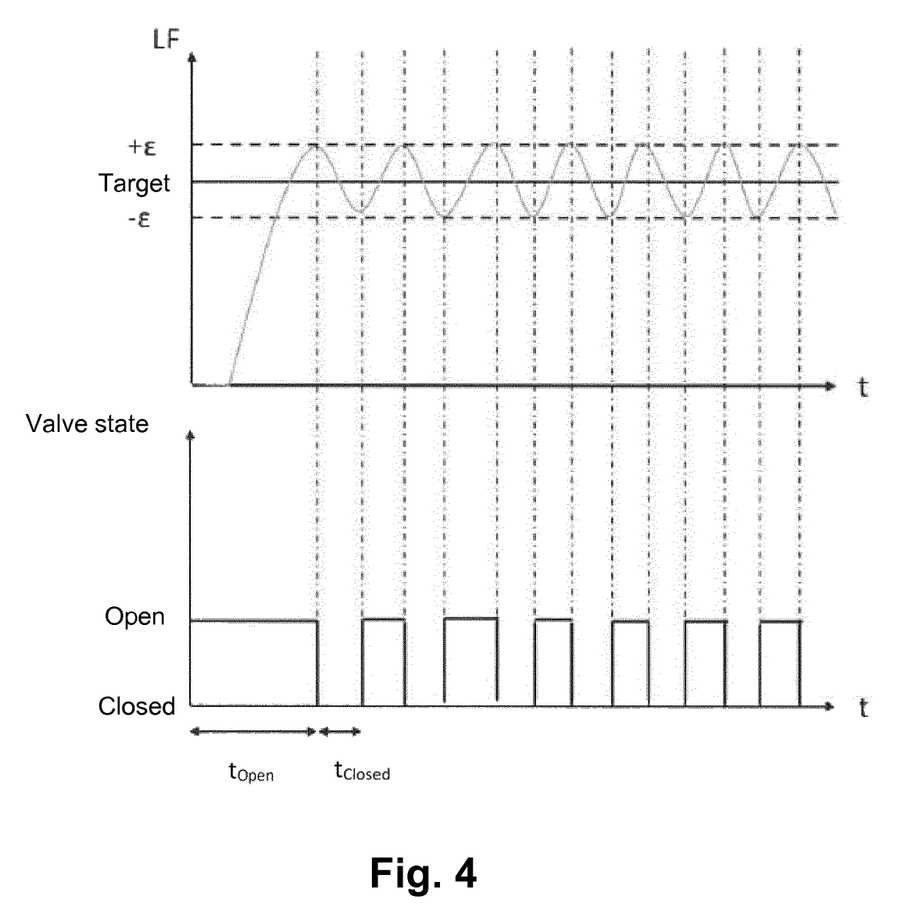
FIG. 4 shows a diagram illustrating an example of the dosing of the basic or acidic fluid according to an aspect of the invention.

FIG. 4 shows a diagram illustrating an example of the dosage or setting of the delivery rate of the basic or acidic fluid. For this purpose, the corresponding switchable valve 10 or 11 is opened until an upper concentration value (conductivity value) +ε is determined by the measuring device 12, and the valve 10 or 11 is closed when the upper concentration value +ε is reached. Then the concentration value (or the conductivity measuring signal) LF drops until a lower concentration value −ε is reached, whereupon the valve 10 or 11 is opened again. The mean value between the upper and lower concentration value +ε, −ε corresponds to the concentration target value, i.e. the concentration with which the corresponding fluid in the fresh dialysis liquid should be present. The control procedure described here will be repeated and the associated data will be stored until the data recorded in this regard (e.g. delivery rate of pump 1, opening and closing times of the valves 10 or 11, concentration values, etc.) allow to determine optimum opening and closing times $t_{Open}$, $t_{Closed}$ of the valves 10 or 11 and based on this the delivery rate can subsequently be controlled (i.e. can be set without further feedback of measurement data). The controller used can be a multi-point controller, in particular a two-point controller, P controller, PI controller, PID controller, fuzzy controller, adaptive controller, hybrid controller and/or a controller based on artificial neural networks.

Figure 5:
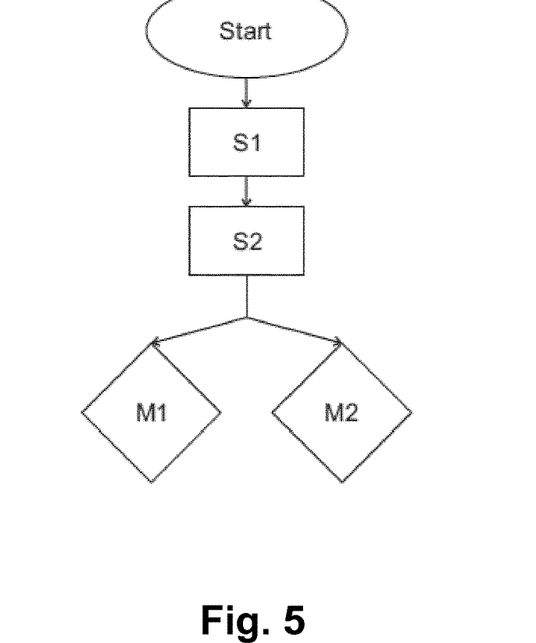
FIG. 5 shows a schematic representation of the method according to an aspect of the invention.

FIG. 5 shows a schematic representation of the (calibration) method according to an aspect of the invention. After the method has been started, at least one physical and/or chemical target value for a water/fluid mixture consisting of water, the basic fluid and/or acidic fluid is first defined, and the corresponding delivery rates of the water, of the basic fluid and/or of the acidic fluid are set. The setting can be done by calculation, analytical determination or another definition. This corresponds to method step S1. Water is then pumped at the set delivery rate. This corresponds to method step S2. Subsequently, the basic fluid and the acidic fluid are conveyed either in a mode M1 or in a mode M2 and introduced into the water. The modes M1 and M2 are described in more detail in the descriptions of FIG. 6 and FIG. 7 below.

Figure 6:
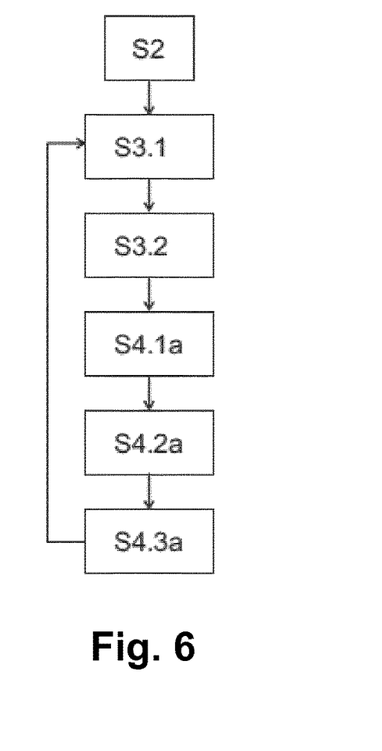
FIG. 6 shows a schematic representation of a first metering mode according to the invention.

FIG. 6 shows a schematic representation of a first mode, according to the invention, of the metering M1 in which the basic fluid and the acidic fluid are alternately/serially pumped and added. Starting from the method step S2, which has been explained in more detail above in the description of FIG. 5, the conveying of only a first one of the basic and acidic fluids (hereinafter first fluid) is started and introduced into the conveyed water. The delivery can be carried out with a set delivery rate for the first fluid, in particular with the delivery rate set in step S1. This corresponds to method step S3.1. Subsequently, at least one physical and/or chemical parameter of the water/fluid mixture, consisting of water and the first fluid or containing these, is measured and the measured value is compared with at least one defined target value provided for the water/fluid mixture and defined in particular in step S1. This corresponds to the method step S3.2. In the subsequent method step S4.1a, upon reaching the at least one target value, the delivery of only the first fluid is stopped and the delivery exclusively of the second one of the basic and acidic fluids (hereinafter second fluid) is started and introduced into the water. The delivery can be carried out with a set delivery rate for the second fluid, in particular with the delivery rate set in step S1. Then, at least one physical and/or chemical parameter of the water/fluid mixture, which consists of water and the acidic fluid or contains these, is measured and the measured value is compared with the at least one defined target value for the water/fluid mixture, in particular defined in step S1, which corresponds to the method step S4.2a. In the subsequent method step S4.3a, upon reaching the at least one target value, the delivery of the second fluid is interrupted and the method is continued with step S3.1 or the steps are repeated from step S3.1 onwards. If the delivery rate for the water, the first fluid and/or the second fluid is to be changed, this can be done by measurement control at any point in time during the method, in which only that component is conveyed whose delivery rate is to be changed.

In the case in which the two fluids are alternately delivered, it should be noted that the corresponding target values for their concentration are each multiplied according to the ratio of the addition time or valve opening time of the individual fluids in such a way that the set addition quantity, averaged over time, leads to the desired concentration of the fluid in the fresh dialysis fluid. For example, if the valve opening time of the basic fluid is the same as the valve opening time of the acidic fluid, the corresponding target values are doubled.

Figure 7:
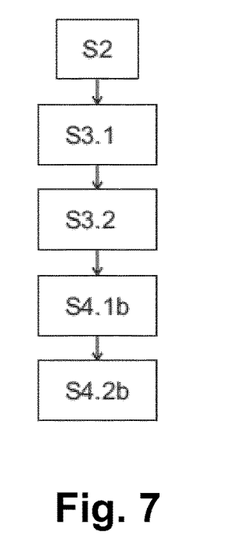
FIG. 7 shows a schematic representation of a second metering mode according to the invention.

FIG. 7 shows a schematic representation of a second mode, according to the invention, of the metering M2 in which the basic fluid and the acidic fluid are delivered and added in parallel in a time-staggered manner. The mode M2 is similar to the mode M1 described above up to and including step S3.2. Starting from method step S3.2, in the subsequent step S4.1b the delivery of the first fluid will be maintained at the previously set delivery rate and the last measured parameter is kept as a reference value if the at least one target value is reached for the water/fluid mixture which consists of water and the first fluid or contains it, whereupon the delivery of the second fluid will be started and the latter is then introduced into the water. Here, the delivery can be performed at a set delivery rate for the second fluid, especially the delivery rate adjusted in step S1. Subsequently, at least one physical and/or chemical parameter of the water/fluid mixture, consisting of water and both fluids or containing them, is measured and the measured value is compared with at least one defined target value or the previously defined reference value, in particular defined in step S1, which corresponds to method step S4.2b.

Figure 8:
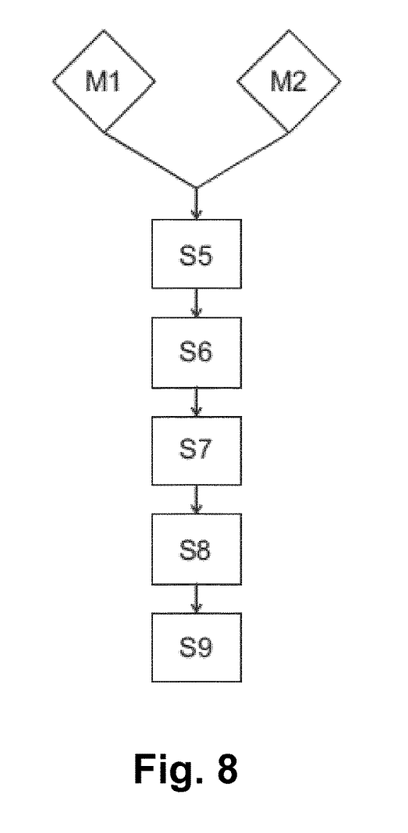
FIG. 8 shows a schematic representation of a mode, according to the invention, of adapting the delivery rate.

FIG. 8 shows a schematic representation of a mode M3, according to the invention, of the delivery rate adaptation. Starting from M2, the delivery rate of a first one of the basic and acidic fluids (hereinafter first fluid) is to be changed. For this purpose, following the mode M2, first the conveying of the second one of the basic and acidic fluids (hereinafter second fluid) is paused, which corresponds to step S5. The first fluid is then delivered at a newly set delivery rate and introduced into the water/fluid mixture. This corresponds to step S6. Subsequently, step S7 is executed, in which at least one physical and/or chemical parameter of the water/fluid mixture, consisting of water and the first fluid or containing it, is measured and compared with the new target value based on the changed delivery rate. Subsequently, when the new target value is reached, the newly set delivery of the first fluids is continued and the delivery of the second fluid is resumed and the latter is introduced into the water. This corresponds to step S8. Subsequently, at least one physical and/or chemical parameter of the fluid mixture, consisting of water and the two fluids or containing them, is measured and compared to at least one defined target value, which corresponds to step S9. The method can then be continued in the mode M1, M2 or M3. Alternatively, in step S5 the conveying of the second fluids can be continued while maintaining the set delivery rate. The steps S7 and S8 are omitted in this alternative.

Figure 9:
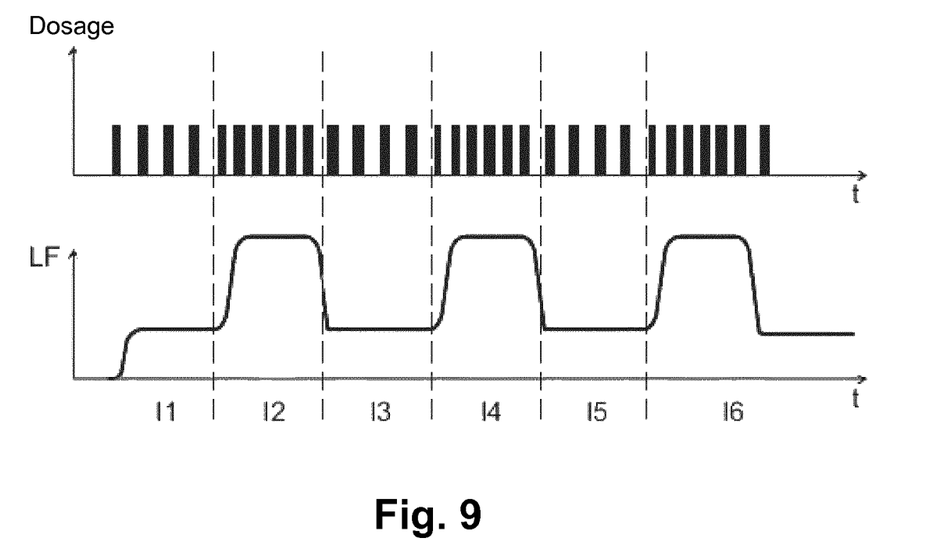
FIG. 9 shows a diagram of a dosing/addition method and a diagram of the recorded measurement signal according to an aspect of the invention.

FIG. 9 shows a diagram of an exemplary dosage/addition method and a diagram of the recorded measurement signal according to an aspect of the invention. In the upper diagram, the bars in the intervals 11, 13 and 15 represent the dosed volumes of the basic fluid. The bars in the intervals 12, 14 and 16 represent the dosed volumes of the acidic fluid. This diagram shows that the dosing of the fluids is performed in a pulsating manner, i.e. the fluid volumes are added intermittently to the first fluid.

In the diagram below, the conductivity of a water/fluid mixture consisting of water, the basic and/or acidic fluid measured at a measuring device is plotted as a function of time. The basic fluid has a lower conductivity than the acidic fluid. So when a volume of acidic fluid is measured at the measuring device, the conductivity signal is higher than when a volume of basic fluid is measured at the measuring device. Therefore, in the intervals in which the acidic fluid is added in pulsating fashion, the measured conductivity is greater than in the intervals in which the basic fluid is added.

Figure 10:
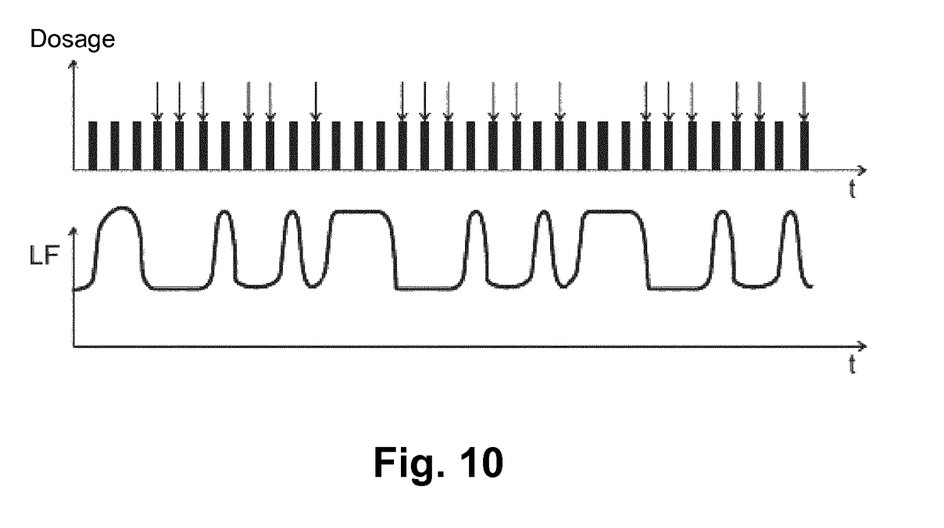
FIG. 10 shows a diagram of a coded dosing/addition method and a diagram of the recorded measurement signal according to an aspect the invention.

FIG. 10 shows a diagram of a coded dosage/addition method and a diagram of the recorded measurement signal according to an aspect of the invention. In the upper diagram, the bars marked with an arrow represent the dosed volumes of the basic fluid and the bars without a mark represent the dosed volumes of the acidic fluid. The coding, as described here, is not limited to the alternating delivery of the basic fluid and acidic fluid (e.g. in mode M1), since the high conductivity ("+1") can also be achieved by maintaining the delivery of the basic fluid when the acidic fluid is added. The signal or reading of the basic fluid can be encoded according to the Barker code with "−1" and the signal or reading of the acidic fluid can be encoded according to the Barker code with "+1". The diagram shows the dosage according to a Barker code having a length of eleven with "+1+1+1−1−1−1+1−1−1+1−1" or "SK SK SK BK BK BK SK BK BK SK BK". Here, "SK" may also be "SK+BK" (e.g. in mode M2).

In the diagram below, the conductivity of a fluid mixture consisting of water, the basic and/or acidic fluid measured at a measuring device is plotted as a function of time. The measured signal corresponds to the Barker code having a length of eleven with "+1+1+1−1−1−1+1−1−1+1−1" or "SK SK SK BK BK BK SK BK BK SK BK", where "SK" may also be "SK+BK" (e.g. in mode M2).

The signal resulting at the measuring device can be processed or evolved by appropriate mathematical means, whereupon conclusions can be drawn about the addition quantities of the individual components. The total signal, for example the total conductivity, can additionally be determined by mathematical averaging. According to this principle, other codings, such as those used in communications engineering, are also conceivable.

From the signal dynamics it can also be concluded whether the functionality of the measuring equipment is still given. Since a calibration to the individual fluids is carried out at the beginning of a conditioning phase, an expected value for a difference and a ratio of the two parameters of the fluids, for example conductivity, is known. Through the mathematical evolution, both measured values, i.e. for a mixture made up of the basic and acidic fluid, can be constantly calculated and set in relation to each other. From the comparison with the original ratio it can be concluded that the measuring device is still functioning. With this method it is also possible to save an existing additional measuring device in state of the art devices.

Figure 11:
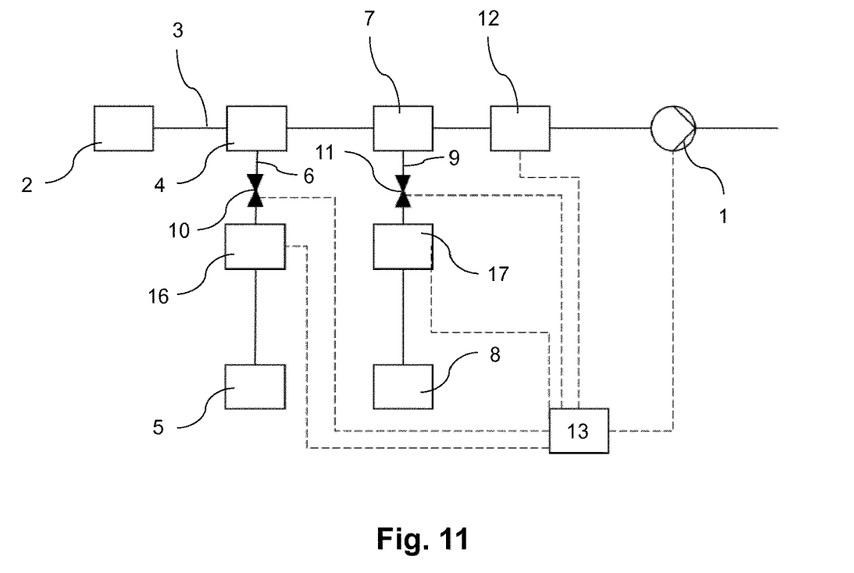
FIG. 11 shows a schematic representation of a third device according to the invention.

FIG. 11 shows a third embodiment according to the invention of the device for the production of a dialysis liquid. The basic structure and the reference numerals from the first embodiment remain unchanged, so that in the following only differences between the first and third embodiment are discussed. In addition to the first embodiment, a pressure sensor 16, 17 is provided respectively upstream, but preferably at the same height of each valve 10, 11. The pressure sensors 16, 17 can be used for determining the type of concentrate supply, i.e. if a canister, a cartridge or a central concentrate supply is actually fluid-connected to the device for extracorporeal blood treatment. In case the first storage container 5 and the second storage container 8 are concentrate canisters, the pressure sensors 16, 17 measure a pressure of ≤0 mmHg when the valves 10, 11 are closed as there is no positive pressure within the canister. If however a cartridge is used as concentrate supply, a positive pressure of approximately 300 mmHg exists under same valve conditions since the cartridge is already pressurized during manufacturing. With a central concentrate supply, the pressure might be even higher and at about 900 mmHg. When the type of concentrate supply is determined by means of the pressure sensors 16, 17, controller properties such as the P-, I- and/or D-part of the controller of the control and regulation unit 13 can be adjusted for dosage of the acidic and basic liquid. Thus, by processing the signals of the measuring device 12 and the pressure sensors 16, 17, the control and regulation unit 13 controls the pump 1 as well as the valves 10, 11.

Figure 12:
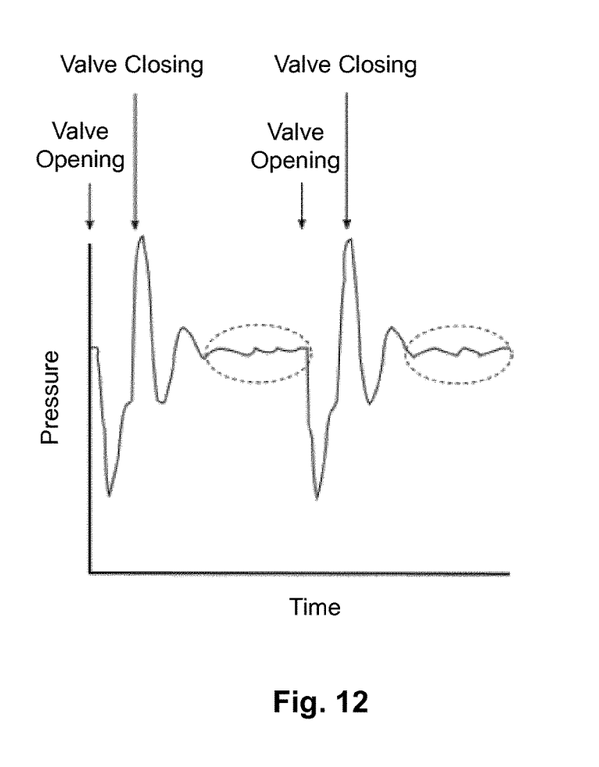
FIG. 12 shows a diagram illustrating a time course of pressure according to an aspect of the invention.

In case a concentrate canister is used as concentrate supply, a filling level $h_F$ of the concentrate contained in the canister can be determined by means of the pressure sensors 16, 17 by evaluating the pressure over time as shown in FIG. 12. After opening of the valve 10, 11 as shown in FIG. 12 the pressure measured deflects until the valve 10, 11 is closed again. After closing of the valve 10, 11 the previous deflection decays and the pressure signal is stabilized. The stabilized or steady state pressure shown in form of dotted line borders in FIG. 12 is preferably averaged (average or median) and referred to as $p_{rel}$. By using the basic equation of hydrostatics (1), the following relationship between $p_{rel}$ and the capillary rise $h_S$, which is defined as the height between the filling level $h_F$ of the concentrate contained in the canister and the pressure sensor 16, 17, can be drawn:

(1)

$$h_g = \frac{p_{rel}}{\rho \cdot g}$$

In this context, ρ stands for the almost constant density and g stands for the gravitational acceleration, which are both known variables. After calculation of the capillary rise $h_S$ based on the previously mentioned basic equation of hydrostatics (1), the filling level $h_F$ of the concentrate contained in the canister can be calculated according to the following equation:

$$h_F = h_{ges} - |h_g| \qquad (2)$$

Figure 13:
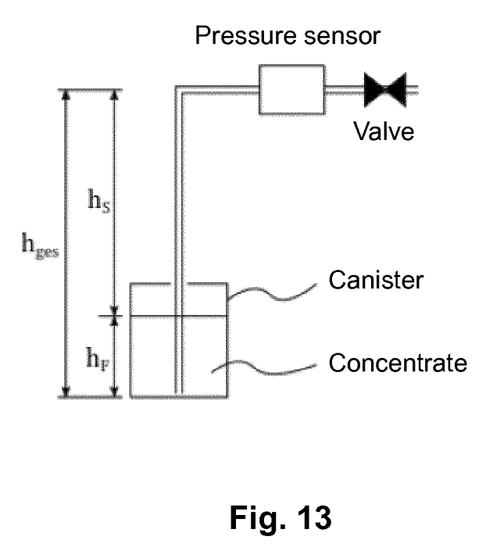
FIG. 13 shows a schematic representation for determining a filling level of a canister that provides one of the concentrates used for producing a dialysis liquid.

With reference to FIG. 13 the above-mentioned equation (2) for calculating the filling level $h_F$ of the concentrate contained in the canister is explained. According to FIG. 13, the filling level $h_F$ of the canister is determined by use of the total height $h_{ges}$ consisting of the capillary rise $h_S$ and the filling level $h_F$ of the canister. By subtracting the previously calculated capillary rise $h_S$ from the total height $h_{ges}$, a conclusion can be drawn over the actual filling level $h_F$ of the concentrate contained in the canister. In this way, it can be determined whether the canister of the connected fluid is empty and needs to be replaced.

The invention claimed is:

1. A method for processing dialysis liquids for use in extracorporeal blood treatment, comprising the steps of:
   conveying water via a main line at a water delivery rate;
   introducing a basic fluid at a basic fluid delivery rate into the main line at a first introduction point formed as a first Venturi mixer;
   introducing an acidic fluid at an acidic fluid delivery rate into the main line at a second introduction point formed as a second Venturi mixer or at the first introduction point formed as the first Venturi mixer, the water, the basic fluid and the acidic fluid forming a water/fluid mixture;
   measuring a first physical and/or chemical parameter of the water/fluid mixture with a first measuring device, the first physical and/or chemical parameter comprising at least one of the water, the acidic fluid and the basic fluid; and
   adjusting the water delivery rate, the acidic fluid delivery rate and/or the basic fluid delivery rate by a control and regulation unit as a function of a measured value detected,
   wherein measurement of the first physical and/or chemical parameter is performed with the first measuring device located at a section of the main line downstream of the second introduction point for the acidic fluid and of the first introduction point for the basic fluid; and
   the control and regulation unit at least temporarily controls the acidic fluid delivery rate and/or the basic fluid delivery rate such that over a predetermined period or a predetermined interval only one of the acidic fluid and the basic fluid is introduced into the main line, wherein the introduction of the basic fluid and the introduction of the acidic fluid take place alternately.

2. The method according to claim 1, wherein the introduction of the basic fluid and the introduction of the acidic fluid take place in continuous alternating fashion.

3. The method according to claim 1, wherein, when an adjustment of a respective delivery rate of one the basic fluid and acidic fluid occurs, a respective delivery rate of the other of the basic fluid and acidic fluid is maintained as set before said adjustment, or the respective introduction of the other of the basic fluid and acidic fluid is paused.

4. The method according to claim 1, wherein the water/fluid mixture is moved past a device for extracorporeal blood treatment when changing or newly setting at least one target value until the at least one target value is reached for a first time at least once.

5. The method according to claim 4, wherein, in a case in which for reaching the at least one target value, a defined period of time is exceeded and/or the basic fluid delivery rate or the acidic fluid delivery rate is set which exceeds a defined limit value, a warning is issued at the device for extracorporeal blood treatment.

6. The method according to claim 1, further comprising:
measuring a second physical and/or chemical parameter of the water/fluid mixture with a second measuring device, the second physical and/or chemical parameter comprising at least one of the water, the basic fluid and/or the acidic fluid, and the second measuring device being arranged on the main line directly downstream of the first measuring device,
wherein a warning is issued at a device for extracorporeal blood treatment when there is a deviation between a first measurement of the first physical and/or chemical parameter and a second measurement of the second physical and/or chemical parameter that exceeds a defined limit value.

7. The method according to claim 1, wherein the water/fluid mixture is intermixed with at least one mixing device provided in addition to the first Venturi mixer or the second Venturi mixer.

8. The method according to claim 7, wherein the at least one mixing device is a chamber of a chamber-based balancing system and a physical and/or chemical target value of the water/fluid mixture is defined such that the physical and/or chemical target value of the water/fluid mixture can be realized mathematically within a unit of time which corresponds at most to one switching process of the chamber.

9. The method according to claim 1, wherein the introduction of the basic fluid and the introduction of the acidic fluid are coded.

10. The method according to claim 1, wherein the first physical and/or chemical parameter of the water/fluid mixture is measured with only one of the basic fluid and the acidic fluid, and based thereon, a first dosage rate of said one of the basic fluid and the acidic fluid is determined, whereupon introduction of said one of the basic fluid and the acidic fluid is interrupted and the other of the basic fluid and the acidic fluid is introduced instead, wherein the first physical and/or chemical parameter of the water/fluid mixture is measured with only the other of the basic fluid and the acidic fluid, and based on this measurement, a second dosage rate of the other of the basic fluid and the acidic fluid is determined and, finally, the one of the basic fluid and the acidic fluid is introduced continuously with the first dosage rate, and the other of the basic fluid and the acidic fluid is introduced continuously with the second dosage rate.

11. A device for performing the method according to claim 1.

12. A device for processing dialysis liquids comprising water, a basic fluid and an acidic fluid, for use in extracorporeal blood treatment, the device comprising:
a main line for supplying the water during which the basic fluid and the acidic fluid are introduced, the basic fluid being introduced at a first dosage by a first Venturi mixer arranged at a first introduction point and the acidic fluid being introduced at a second dosage by a second Venturi mixer arranged at a second introduction point or by the first Venturi mixer arranged at the first introduction point, forming a water/fluid mixture, wherein each of the first dosage and the second dosage is set by a control and regulation unit as a function of a first chemical and/or physical parameter of the water/fluid mixture, and the first chemical and/or physical parameter is detected by a first measuring device wherein:
the first measuring device is arranged at a section of the main line which is positioned downstream of the first introduction point and the second introduction point, and the control and regulation unit at least temporarily controls the introduction of the acidic fluid and the introduction of the basic fluid in such a manner that only one of the acidic fluid and the basic fluid is introduced into the main line over a predetermined period or a predetermined interval,
wherein
the control and regulation unit is adapted to control the introduction of the basic fluid and the introduction of the acidic fluid such that the introduction of the basic fluid and the introduction of the acidic fluid take place alternately.

13. The device according to claim 12, wherein the basic fluid is introduced to the main line by negative pressure generated by the first Venturi mixer and/or the acidic fluid is introduced to the main line by negative pressure generated by the second Venturi mixer.

14. The device according to claim 12, wherein the introduction of the acidic fluid and/or the introduction of the basic fluid is effected by at least one controllable valve.

15. The device according to claim 12, further comprising a second measuring device directly downstream of the first measuring device, the second measuring device adapted to detect a second physical and/or chemical parameter of the water/fluid mixture flowing through the main line.

16. The device according to claim 15, wherein the device comprises, in addition to the first Venturi mixer and second Venturi mixer, at least one mixing device arranged downstream of the first measuring device and the second measuring device.

17. The device according to claim 12, wherein:
the control and regulation unit is configured to control the introduction of the acidic fluid and/or the introduction of the basic fluid during a control operation such that over a predetermined period or a predetermined interval only one of the acidic fluid and the basic fluid is introduced into the main line; and
the control and regulation unit is configured to set a continuous introduction rate of the acidic fluid and/or a continuous introduction rate of the basic fluid as soon as the control operation is completed.

18. The device according to claim 14, wherein at least one pressure sensor is provided upstream of the at least one controllable valve for determining a type of concentrate supply fluid-connected to the device.

19. The device according to claim 18, wherein, when a concentrate canister is determined as the type of concentrate supply fluid-connected to the device, the control and regulation unit is adapted to determine a filling level of a concentrate contained in the concentrate canister by communication with the at least one pressure sensor.

20. The device according to claim 19, wherein the device is adapted to issue a haptic, acoustic or visual warning signal if the filling level of the concentrate contained in the concentrate canister falls below a previously set threshold value.

21. The device according to claim 12, wherein the control and regulation unit is adapted to control the introduction of the basic fluid and the introduction of the acidic fluid such that the introduction of the basic fluid and the introduction of the acidic fluid take place in continuous alternating fashion.

\* \* \* \* \*